(12) United States Patent
Roscoe et al.

(10) Patent No.: US 9,987,633 B2
(45) Date of Patent: Jun. 5, 2018

(54) ASSAY DEVICES AND METHOD OF DETECTING A TARGET ANALYTE

(71) Applicant: 3M INNOVATIVE PROPERTIES COMPANY, St. Paul, MN (US)

(72) Inventors: Stephen B. Roscoe, Woodbury, MN (US); Myungchan Kang, Woodbury, MN (US); Evan D. Brutinel, Inver Grove Heights, MN (US); Jesse D. Miller, Ann Arbor, MI (US); Renee K. Cline, Blaine, MN (US); Minghua Dai, Plymouth, MN (US); Hsi-Chou Liu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 15/309,505

(22) PCT Filed: Jun. 8, 2015

(86) PCT No.: PCT/US2015/034624
§ 371 (c)(1),
(2) Date: Nov. 8, 2016

(87) PCT Pub. No.: WO2015/191419
PCT Pub. Date: Dec. 17, 2015

(65) Prior Publication Data
US 2017/0128935 A1 May 11, 2017

Related U.S. Application Data

(60) Provisional application No. 62/009,602, filed on Jun. 9, 2014.

(51) Int. Cl.
*B01L 3/00* (2006.01)
*G01N 33/53* (2006.01)

(52) U.S. Cl.
CPC ........ *B01L 3/5029* (2013.01); *G01N 33/5304* (2013.01); *B01L 2200/16* (2013.01);
(Continued)

(58) Field of Classification Search
CPC ..................... B01L 3/5029; G01N 33/5304
See application file for complete search history.

(56) References Cited

U.S. PATENT DOCUMENTS

| | | |
|---|---|---|
| 4,353,868 A | 10/1982 | Joslin |
| 5,215,102 A | 6/1993 | Guirguis |

(Continued)

FOREIGN PATENT DOCUMENTS

| | | |
|---|---|---|
| CN | 101893523 | 11/2010 |
| JP | 06-504130 | * 5/1994 |

(Continued)

OTHER PUBLICATIONS

International Search Report for PCT International Application No. PCT/US2015/034624 dated Mar. 8, 2016, 4 pages.

*Primary Examiner* — Melanie Yu Brown
(74) *Attorney, Agent, or Firm* — Adrian L. Pishko

(57) ABSTRACT

Assay devices are provided including a receptacle having a sample entry port; a plunger disposed within the receptacle; at least one reagent; a membrane attached to a first surface of the plunger; a wick providing capillary force; and a detection zone. The membrane includes a target conjugate zone in which affinity components are disposed. Capture compounds are immobilized in a detection zone, which is located between the target conjugate zone and the wick. A method of detecting a target analyte is also provided, including providing the assay device; providing a sample suspected to contain a target analyte; adding the sample onto the device; allowing the sample to travel along the membrane until the sample reaches the detection zone; immobilizing (Continued)

the target analyte through reaction of the target analyte with the capture compounds; reacting the immobilized target analyte with a reagent to generate a detectable signal; and detecting the generated signal.

7 Claims, 7 Drawing Sheets

(52) U.S. Cl.
CPC .................. *B01L 2300/0825* (2013.01); *B01L 2400/0406* (2013.01); *B01L 2400/0478* (2013.01)

(56) References Cited

U.S. PATENT DOCUMENTS

| | | | |
|---|---|---|---|
| 5,514,120 | A | 5/1996 | Johnston |
| 5,728,446 | A | 3/1998 | Johnston |
| 5,783,399 | A | 7/1998 | Childs |
| 5,869,003 | A | 2/1999 | Nason |
| 5,879,635 | A | 3/1999 | Nason |
| 5,965,453 | A | 10/1999 | Skiffington |
| 5,989,921 | A | 11/1999 | Charlton |
| 6,080,243 | A | 6/2000 | Insley |
| 6,290,685 | B1 | 9/2001 | Insley |
| 6,316,205 | B1 | 11/2001 | Guan |
| 6,372,954 | B1 | 4/2002 | Johnston |
| 6,381,846 | B2 | 5/2002 | Insley |
| 6,420,622 | B1 | 7/2002 | Johnston |
| 6,485,982 | B1 | 11/2002 | Charlton |
| 6,524,530 | B1 | 2/2003 | Igarashi |
| 6,531,206 | B2 | 3/2003 | Johnston |
| 6,548,018 | B2 | 4/2003 | DiCesare |
| 6,653,147 | B2 | 11/2003 | DiCesare |
| 6,663,833 | B1 | 12/2003 | Stave |
| 6,746,567 | B2 | 6/2004 | Johnston |
| 6,803,090 | B2 | 10/2004 | Castiglione |
| 6,881,554 | B2 | 4/2005 | DiCesare |
| 6,887,681 | B2 | 5/2005 | DiCesare |
| 6,907,921 | B2 | 6/2005 | Insley |
| 7,060,223 | B2 | 6/2006 | DiCesare |
| 7,308,803 | B2 | 12/2007 | Brokaw |
| 7,399,984 | B2 | 7/2008 | Feldsine |
| 7,485,262 | B2 | 2/2009 | DiCesare |
| 7,780,915 | B2 | 8/2010 | Gao |
| 7,909,264 | B2 | 3/2011 | Dunne |
| 8,192,943 | B2 | 6/2012 | Harris |
| 8,377,379 | B2 | 2/2013 | Feaster |
| 8,697,374 | B2 | 4/2014 | Rajagopal |
| 2003/0064526 | A1 | 4/2003 | Niedbala |
| 2005/0106360 | A1 | 5/2005 | Johnston |
| 2006/0263907 | A1 | 11/2006 | Zweig |
| 2008/0145272 | A1 | 6/2008 | Feaster |
| 2009/0242048 | A1 | 10/2009 | Sherman |
| 2010/0099127 | A1* | 4/2010 | Bodner ................ B01L 3/5029 435/22 |
| 2011/0117673 | A1 | 5/2011 | Johnson |
| 2011/0165589 | A1 | 7/2011 | Biesbrouck |
| 2011/0306151 | A1 | 12/2011 | Murphy |
| 2014/0227796 | A1* | 8/2014 | Gold .................... B01L 3/5029 436/501 |

FOREIGN PATENT DOCUMENTS

| | | |
|---|---|---|
| WO | WO 1997-23596 | 7/1997 |
| WO | WO 1999-46591 | 9/1999 |
| WO | WO 2001-55723 | 8/2001 |
| WO | WO 2006-119203 | 11/2006 |
| WO | WO 2007-016691 | 2/2007 |
| WO | WO 2007-098184 | 8/2007 |
| WO | WO 2010-092333 | 8/2010 |
| WO | WO 2012-078455 | 6/2012 |
| WO | WO 2012-103511 | 8/2012 |
| WO | WO 2012-161744 | 11/2012 |
| WO | WO 2013-134745 | 9/2013 |
| WO | WO 2015-164632 | 10/2015 |

* cited by examiner

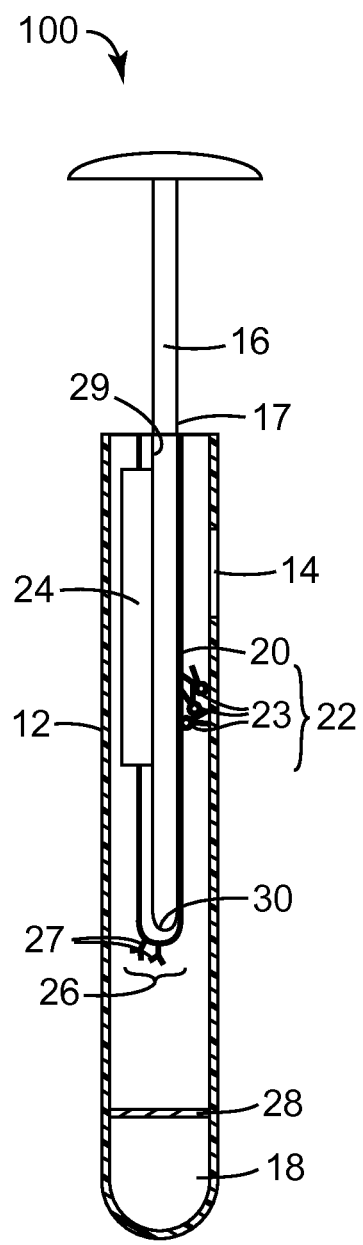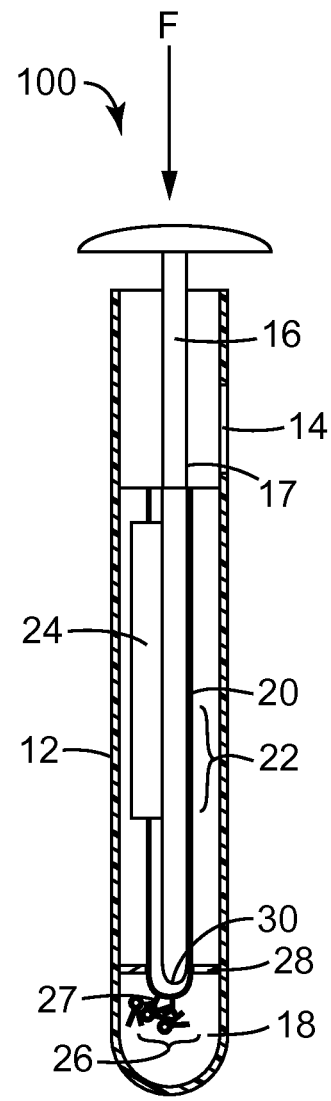
*FIG. 1A*  *FIG. 1B*

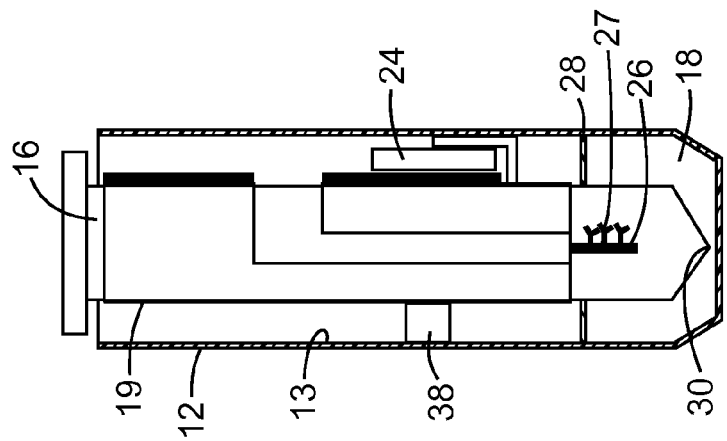
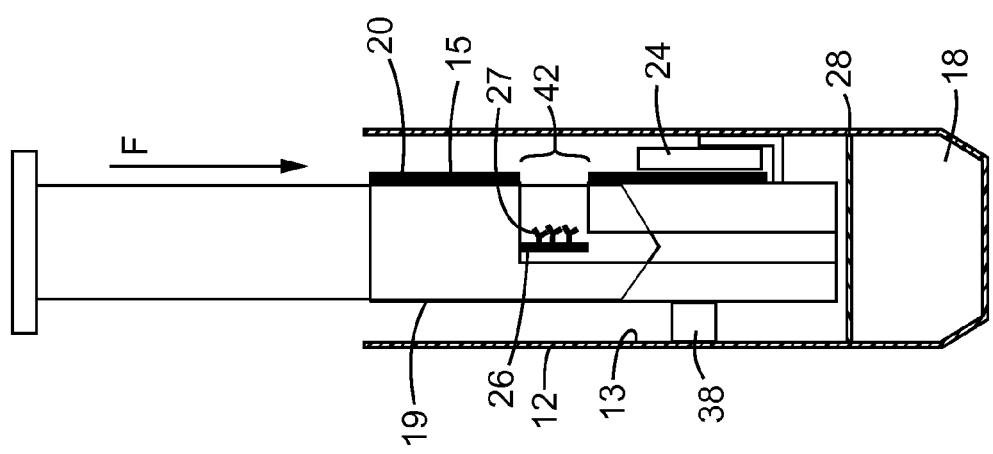
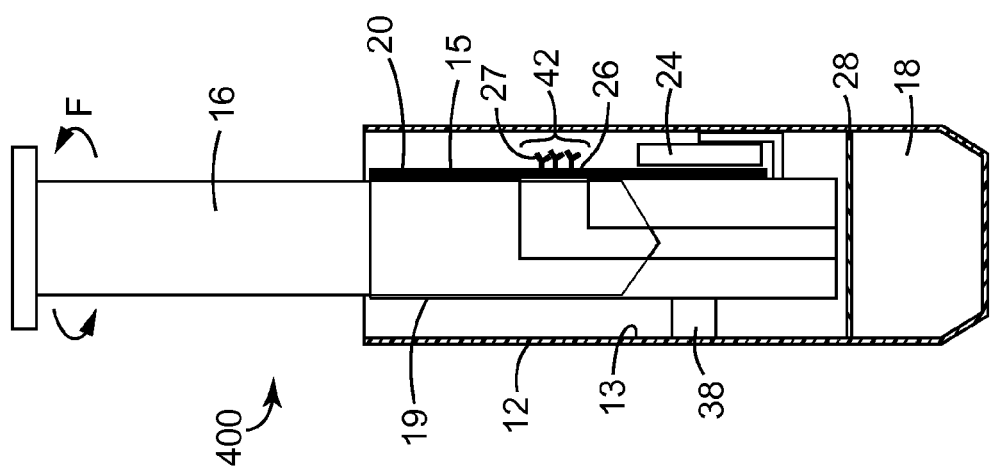

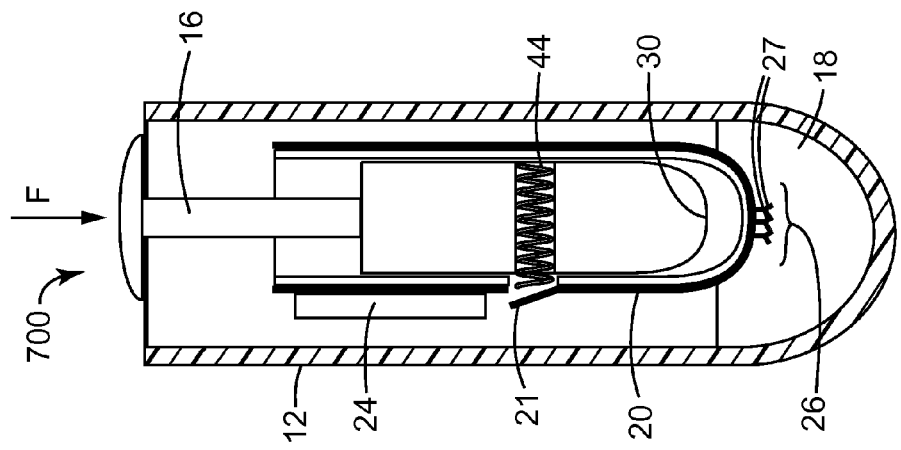
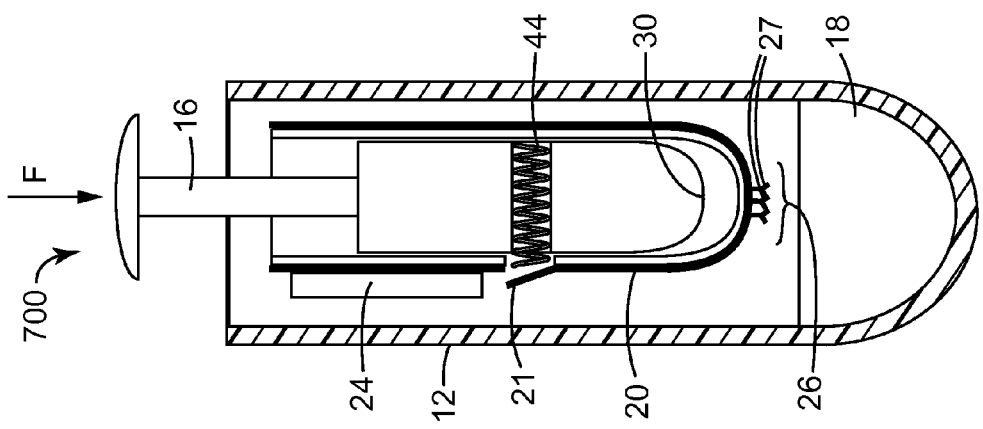
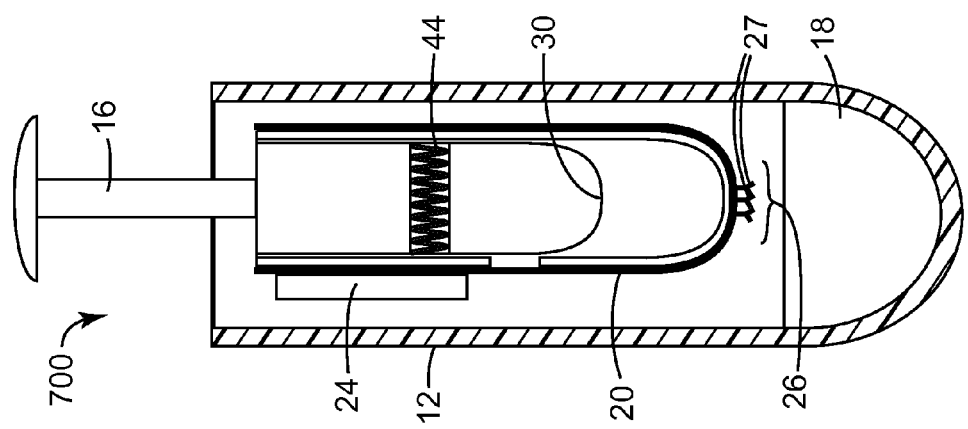

ASSAY DEVICES AND METHOD OF DETECTING A TARGET ANALYTE

CROSS REFERENCE TO RELATED APPLICATIONS

This application is a national stage filing under 35 U.S.C. 371 of PCT/US2015/034624, filed Jun. 8, 2015, which claims the benefit of U.S. Application No. 62/009,602, filed Jun. 9, 2014, the disclosure of which is incorporated by reference in its/their entirety herein.

FIELD

Assay devices and methods of detecting target analytes are provided including quantitative test results, such as using chemiluminescence, fluorescence, colorimetry, etc.

BACKGROUND

Lateral flow immunoassays are widely used in the food and medical diagnostics industries, as well as in simple point-of-care tests such as rapid strep tests and pregnancy tests. The lateral flow strip itself is usually a surfactant-infused nitrocellulose membrane, which contributes variability to the device results. Current technology for immunoassays is typically non-quantitative and lacks sensitivity.

Hence, there remains a need for an assay device that provides a rapid test result while also providing quantitative results.

SUMMARY

Assay devices and methods of detecting a target analyte are provided. In a first aspect, an assay device is provided. More particularly, an assay device is provided including a receptacle including a sample entry port; a plunger disposed within the receptacle and having a first surface; at least one reagent; a membrane attached to the first surface of the plunger; a wick providing capillary force; and a detection zone. The membrane includes a target conjugate zone in which a plurality of affinity components are disposed. A plurality of capture compounds are immobilized in a detection zone, which is located between the target conjugate zone and the wick.

In a second aspect, another assay device is provided. The assay device includes a receptacle including a surface and a sample entry port; a membrane attached to the surface of the receptacle; at least one reagent disposed in the receptacle; a plunger disposed within the receptacle and having a surface; and a detection zone in which a plurality of capture compounds are immobilized. The membrane has a wick providing capillary force. The detection zone is attached to the surface of the plunger and is located between the sample entry port and the wick.

In a third aspect, a method of detecting a target analyte is provided. The method includes (a) providing an assay device including a receptacle including a surface and a sample entry port; at least one reagent; a plunger disposed within the receptacle and having a surface; a membrane attached to the surface of the plunger, the surface of the receptacle, or both; and a detection zone in which a plurality of capture compounds are immobilized. The membrane includes a wick providing capillary force, and the detection zone is located between the sample entry port and the wick. The method further includes (b) providing a sample suspected to contain a target analyte; (c) adding the sample onto the membrane through the sample entry port; (d) allowing the sample to travel along the membrane until the sample reaches the detection zone; (e) immobilizing the target analyte through reaction of the target analyte with the capture compounds; (f) reacting the immobilized target analyte with the at least one reagent to generate a detectable signal; and (g) detecting the generated signal.

Use of the assay devices and methods allows for simple, rapid, quantitative assay testing of target analytes.

BRIEF DESCRIPTION OF THE DRAWINGS

FIG. 1A is an exemplary partial cross-sectional schematic of an assay device.

FIG. 1B is an exemplary partial cross-sectional schematic of the assay device of FIG. 1A following depression of the plunger.

FIG. 4A is a still further exemplary partial cross-sectional schematic of an assay device.

FIG. 4B is an exemplary partial cross-sectional schematic of the assay device of FIG. 4A following rotation of the plunger.

FIG. 4C is an exemplary partial cross-sectional schematic of the assay device of FIG. 4B following depression of the plunger.

FIG. 7A is a still further exemplary partial cross-sectional schematic of an assay device.

FIG. 7B is an exemplary partial cross-sectional schematic of the assay device of FIG. 7A following an initial depression of the plunger.

FIG. 7C is an exemplary partial cross-sectional schematic of the assay device of FIG. 7B following a further depression of the plunger.

Figure 2A:
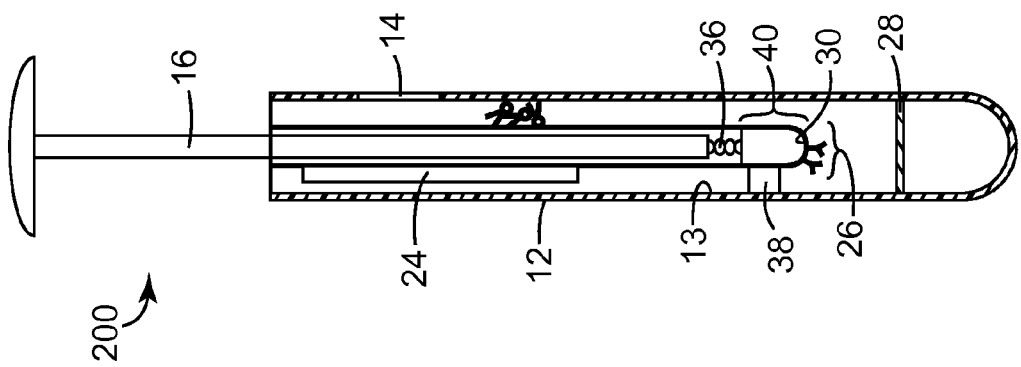
FIG. 2A is another exemplary partial cross-sectional schematic of an assay device.

While the above-identified drawings, which may not be drawn to scale, set forth various embodiments of the present disclosure, other embodiments are also contemplated, as noted in the Detailed Description.

DETAILED DESCRIPTION

Assay devices and methods of detecting a target analyte are provided.

The recitation of any numerical range by endpoints is meant to include the endpoints of the range, all numbers within the range, and any narrower range within the stated range (e.g. 1 to 5 includes 1, 1.5, 2, 2.75, 3, 3.8, 4, and 5). Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described.

The term "and/or" means either or both. For example, the expression "A and/or B" means A, B, or a combination of A and B.

The term "antibody" refers to an immunoglobulin molecule that reacts with a specific antigen, such as a target analyte, and further refers to an antibody fragment (e.g., ScFv or Fab).

The term "antigen" refers to any substance capable of inducing a specific immune response and of reacting with the products of that response.

The term "aptamer" refers to a DNA or RNA molecule or a peptide that binds to a specific target analyte molecule or atom.

The term "ligand" refers to an atom, molecule, functional group, or ion that is bound to a target analyte molecule or atom, thereby forming a complex.

The term "affinity component" refers to a material that binds to a target analyte, for instance an antibody, aptamer, or ligand for the target analyte. The affinity component is made up of a binding portion and a detection portion. The binding portion includes an antibody, a nucleotide aptamer, a peptide aptamer, or a ligand. The detection portion includes an enzyme, a catalyst, and/or a molecule that provides an optical signal (e.g., a colorimetric signal, a fluorescent signal, or a luminescent signal).

The term "capture compound" refers to a material that binds to a target analyte, for instance an antibody, aptamer, or ligand for the target analyte, and is immobilized to bind the target analyte in place.

Analytes of interest, for example bacteria, proteins, and other atoms or molecules, are often not inherently chemiluminescent, fluorescent, colored, etc., thus in order to achieve specific detection it is necessary to incorporate an affinity component into the assay device, such as an antibody, ligand or aptamer, that will allow the isolation of the analyte and its subsequent detection by a reaction.

In a first aspect, an assay device is provided, comprising:
a receptacle including a sample entry port;
a plunger disposed within the receptacle and having a first surface;
at least one reagent;
a membrane attached to the first surface of the plunger, the membrane comprising:
   a target conjugate zone in which a plurality of affinity components are disposed;
   a wick providing capillary force; and
   a detection zone in which a plurality of capture compounds are immobilized, wherein the detection zone is located between the target conjugate zone and the wick.

Referring to FIG. 1A, in an exemplary embodiment an assay device 100 comprises a receptacle 12 comprising a sample entry port 14; a plunger 16 disposed within the receptacle 12 and having a first surface 17; at least one reagent 18; a membrane 20 attached to the first surface 17 of the plunger 16, the membrane comprising a target conjugate zone 22 in which a plurality of affinity components 23 are disposed; a wick 24 providing capillary force; and a detection zone 26 in which a plurality of capture compounds 27 are immobilized. The detection zone 26 is located between the target conjugate zone 22 and the wick 24. In certain embodiments, the at least one reagent 18 is disposed in the receptacle 12 and the receptacle 12 further comprises a barrier 28 to separate the at least one reagent 18 from the plunger 16. Optionally, the barrier comprises a metal foil or a pouch, for instance a pouch inside of which at least one reagent is disposed. In certain embodiments, the plunger is secured in the receptacle using a compression fitting, glue, or a ridge formed on the interior of the receptacle wall.

Referring to FIG. 1B, when a force F is applied to the plunger 16, the plunger 16 is configured to detach the detection zone 26 from being in fluid communication with the wick 24 and place the detection zone 26 in fluid communication with the at least one reagent 18. In certain embodiments, the plunger 16 comprises an end 30 configured to pierce the barrier 28, such as a pointed end. The configuration of the end of the plunger can vary depending on the thickness and type of material of the barrier. In the embodiment illustrated in FIG. 1B, the barrier 28 is a foil pouch and the end 30 of the plunger 16 is rounded.

In a second aspect, an assay device is provided, comprising:
a receptacle comprising a surface and a sample entry port;
a membrane attached to the surface of the receptacle, the membrane comprising a wick providing capillary force;
at least one reagent disposed in the receptacle;
a plunger disposed within the receptacle and having a surface; and
a detection zone in which a plurality of capture compounds are immobilized, the detection zone attached to the surface of the plunger; wherein the detection zone is located between the sample entry port and the wick.

Figure 5A:
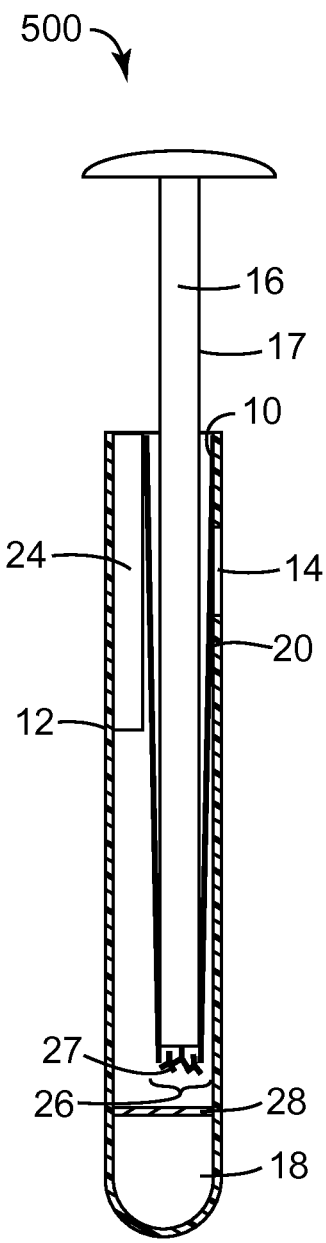
FIG. 5A is yet another exemplary partial cross-sectional schematic of an assay device.
Figure 5B:
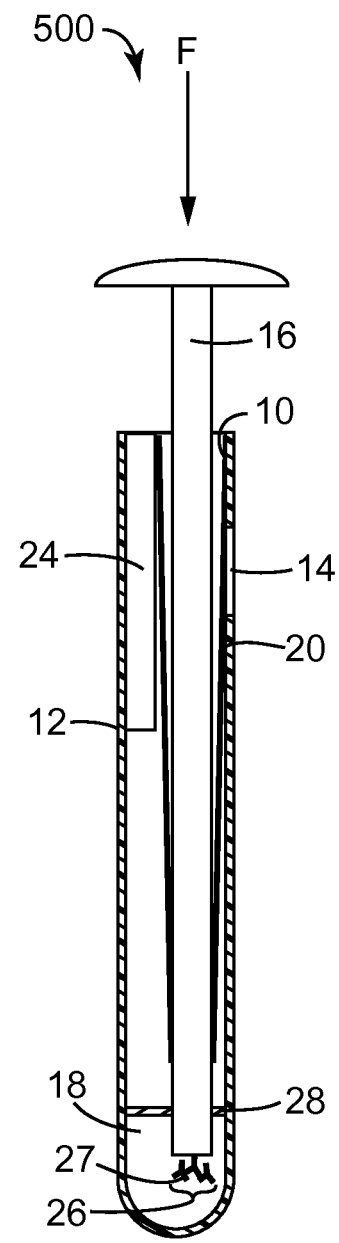
FIG. 5B is an exemplary partial cross-sectional schematic of the assay device of FIG. 5A following depression of the plunger.

Referring to FIGS. 5A and 5B, an assay device 500 is illustrated. The assay device 500 comprises a receptacle 12 comprising a surface 10 and a sample entry port 14; a membrane 20 attached to the surface 10 of the receptacle 12, the membrane 20 comprising a wick 24 providing capillary force; at least one reagent 18 disposed in the receptacle 12; a plunger 16 disposed within the receptacle 12 and having a surface 17; and a detection zone 26 in which a plurality of capture compounds 27 are immobilized, the detection zone 26 attached to the surface 17 of the plunger 16; wherein the detection zone 26 is located between the sample entry port 14 and the wick 24. When a force F is applied to the plunger 16, the detection zone 26 is moved from being in fluid communication with the membrane 20 to being in fluid communication with the at least one reagent 18.

An advantage to the assay devices 100 and 500 illustrated in FIGS. 1A-1B and 5A-5B, respectively, is that a single and simple force F (i.e., depression of the plunger 16), is capable of moving the detection zone 26 from being in fluid communication with the membrane 20 to being in fluid communication with the at least one reagent 18. Moreover, in the assay device 500 of FIGS. 5A-5B, there is no direct path for the at least one reagent 18 to be transported up to the wick 24, and thus background signal from the at least one reagent 18 reacting with excess affinity compound will be avoided.

The below disclosure relates to both the first aspect and the second aspect provided above.

The affinity components employed in the assay devices disclosed herein are not particularly limited as long as they will bind to the target analyte(s) of interest and are capable of participating in a detection reaction. The affinity components comprise any combination of a binding portion with a detection portion. As noted above, the binding portion includes an antibody, a nucleotide aptamer, a peptide aptamer, or a ligand, and the detection portion includes an enzyme, a catalyst, and/or a molecule that provides an optical signal (e.g., a colorimetric signal, a fluorescent signal, or a luminescent signal). Some suitable detection portions of affinity components include for example and without limitation, horseradish peroxidase, luciferase, and alkaline phosphatase. Similar to the affinity components, the capture compounds are not limited as long as they will both remain fixed in place in the detection zone and bind to the target analyte(s) of interest. The capture compounds typically comprise an aptamer, a peptide, an antibody, a ligand, or a combination thereof.

To generate a detectable signal (e.g., light from a chemiluminescent or fluorescent reaction, light absorbance from colorimetry, etc.), any captured analyte(s) and their bound affinity components are reacted with at least one reagent. In many embodiments, the at least one reagent comprises hydrogen peroxide and/or luciferin. Preferably, the at least one reagent comprises an aqueous solution. Luminol is often employed with chemiluminescent reactions involving hydrogen peroxide, thus in certain aspects of the disclosure, the barrier comprises a pouch and the pouch contains luminol. One suitable pouch comprises a cup structure having two plastic rings with a layer of foil affixed to and covering each ring, to form an enclosed cup. The pouch prevents the luminol and hydrogen peroxide from reacting prior to the addition of the captured target analyte, but once the pouch is pierced, the luminol is allowed to contact the hydrogen peroxide. In certain embodiments, the affinity components comprise an enzyme conjugated to an aptamer or an enzyme conjugated to an antibody. The skilled practitioner can identify aptamers and antibodies for specific target analytes of interest. Common enzymes include for example horseradish peroxidase and luciferase. In aspects including the horseradish peroxidase enzyme conjugated to an aptamer or antibody, the quantitative determination of a target analyte will result from the amount of conjugated horseradish peroxidase that reacts with luminol and hydrogen peroxide, for instance. An advantage of the use of the membrane in the receptacle, is that it minimizes background signal by removing excess reaction catalyst (e.g., horseradish peroxidase) via continued travel of the catalyst in solution by capillary action towards the wick and away from the at least one reagent.

The membrane optionally comprises one or more materials typically employed in flow assays, for example and without limitation, a fluid control film, a capillary fluid conductor (e.g., a stack of fluid control films), nitrocellulose, or other nonwoven membranes, such as membranes made of nylon, polysulfone, polyethersulfone, or polyvinylidenedifluoride (PVDF). Suitable nitrocellulose and PVDF membranes, for example, are known to the skilled practitioner, and are commercially available from suppliers such as Bio-Rad Laboratories, Inc. (Hercules, Calif.). The detection zone of a membrane optionally comprises a nonwoven membrane or similar material having a tortuous flow path to maximize contact between the target analyte in a sample solution and the capture compound.

A fluid control film comprises a sheet having at least one microstructure-bearing surface with one or more channels therein that permits, promotes, or facilitates control or directional flow of a liquid. Suitable fluid control films are described in U.S. Pat. Nos. 5,514,120; 5,728,446; 6,080,243; and 6,290,685. Fluid control films are typically in the form of sheets or films rather than a mass of fibers. The channels of fluid control films provide more effective liquid flow than is generally achieved with webs, foam, or tows formed from fibers. The walls of channels formed in fibers will exhibit relatively random undulations and complex surfaces that interfere with flow of liquid through the channels. In contrast, the channels are precisely replicated from a predetermined pattern and form a series of individual open capillary channels that extend along a major surface. These microreplicated channels formed in sheets, films, or tubes are preferably uniform and regular along substantially each channel length and more preferably from channel to channel. Fluid typically wicks up fluid control films a distance of about 2.5 inches (6.35 cm) within approximately 15 seconds. Advantages of employing a fluid control film as compared to a nonwoven membrane include a more even flow path, and thus more reproducible results.

Fluid control films can be formed from any thermoplastic materials suitable for casting, or embossing including, for example, polyolefins, polyesters, polyamides, poly(vinyl chloride), polyether esters, polyimides, polyesteramide, polyacrylates, polyvinylacetate, hydrolyzed derivatives of polyvinylacetate, etc., or combinations thereof. Polyolefins are commonly employed, particularly polyethylene or polypropylene, blends and/or copolymers thereof, and copolymers of propylene and/or ethylene with minor proportions of other monomers, such as vinyl acetate or acrylates such as methyl and butylacrylate. Polyolefins exhibit excellent physical properties, ease of processing, and typically lower cost than other thermoplastic materials having similar characteristics. Polyolefins readily replicate the surface of a casting or embossing roll. They are tough, durable and hold their shape well, thus making such films easy to handle after the casting or embossing process. Hydrophilic polyurethanes also have advantageous physical properties and inherently high surface energy. Alternatively, fluid control films can be cast from thermosets (curable resin materials) such as polyurethanes, acrylates, epoxies and silicones, and cured by exposure to heat or UV or E-beam radiation, or moisture. These materials may contain various additives including surface energy modifiers (such as surfactants and hydrophilic polymers), plasticizers, antioxidants, pigments, release agents, antistatic agents and the like. Suitable fluid control films also can be manufactured using pressure sensitive adhesive materials. In some cases the channels may be formed using inorganic materials (e.g., glass, ceramics, or metals). Preferably, the fluid control film substantially retains its geometry and surface characteristics upon exposure to liquids.

In many embodiments, the plunger of the assay device further comprises a second surface opposite the first surface and an end in communication with the first surface and the second surface, wherein the membrane is in contact with the end and with the second surface. For instance, FIG. 1A illustrates a second surface 29 of the plunger 16 opposite the first surface 17 of the plunger 16 and an end 30 in communication with the first surface 17 and the second surface 29, wherein the membrane 20 is in contact with the end 30 and with the second surface 29. In the embodiment shown in FIG. 1A, the membrane 20 comprises a U-shape around the plunger 16. Other shapes of the membrane are also contemplated, such as a V-shape, a squared-off U shape, and the like. Often, the detection zone of the membrane is located at the end of the plunger. Referring to each of FIGS. 1A, 2A, 3A, 5A, and 6A, having a detection zone 26 located at the end 30 of the plunger 16 places the detection zone in relatively close proximity to the at least one reagent. In certain aspects, the receptacle 12 comprises a test tube or a shape similar to a test tube. When the assay device is placed in a meter such as a 3M CLEAN-TRACE NG Luminometer (available from 3M Company, St. Paul, Minn.), the end 30 of the plunger 16 will be in proximity to the detection zone of the luminometer.

In certain embodiments, the assay device further includes a component (not shown) for assisting in piercing a barrier, for instance a shuttle as described in published international patent application WO 97/23596. The component includes one or more of: a pointed end, at least one projection on the end, and at least one aperture in a surface of the component. Typically, such a component would be advantageously employed when the end of the plunger is rounded or squared-off or the detection zone is located at the end of the plunger. An exemplary configuration of an assay device having such a component includes the component disposed between the bottom of the plunger and the barrier above the reagent solution. The component may be separately movable to break the barrier, or may be attached to the plunger so that when the plunger is manipulated the component pierces the barrier in advance of the plunger reaching the barrier. In certain embodiments, the component is coated with, or otherwise contains, a solid reagent to be added to the reaction mixture when the component breaks the barrier and comes into contact with the reagent solution.

Figure 3A:
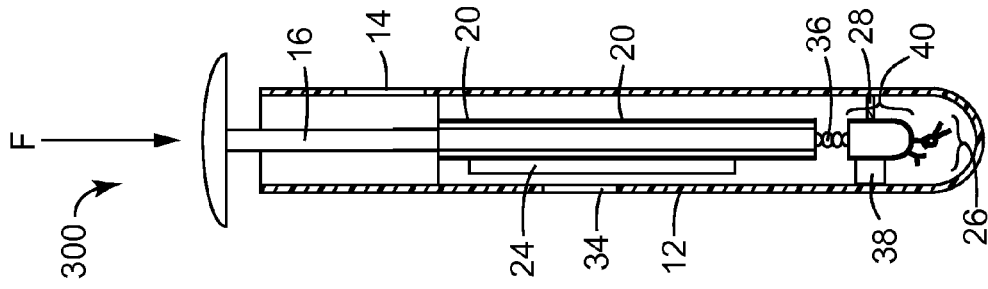
FIG. 3A is a further exemplary partial cross-sectional schematic of an assay device.

Optionally, the membrane further comprises a control line disposed between the wick and the detection zone, the control line comprising a generic capture compound. Referring to FIG. 3A, the assay device 300 is illustrated to include a control line 32 on the membrane 20 between the wick 24 and the detection zone 26. The generic capture compound typically provides a color change when excess affinity component reacts with the generic capture compound. The control line may be easily viewed through a window 34, which allows a user to determine visibly if the sample has traveled past the detection zone and any captured target analyte is ready to be detected. Alternatively, the wick 24 (all or part) could be treated with a weakly buffered solution of a pH indicator. For example, bromophenol blue undergoes a yellow to blue transition as the pH increases from 3 to 5. For any samples that will have a pH of 5 or above once buffered, the appearance of a blue color will function as a sign the sample is ready for detection of any captured target analyte.

FIGS. 3A-3C and 2A-2C further illustrate an assay device 300 and an assay device 200, respectively, including a plunger 16 that contains a threaded lower section 36. The threaded lower section 36 is mounted to an aligner 38 connected to a wall 13 of the receptacle 12 so that when the plunger 16 is rotated about its vertical axis a lower portion 40 of the membrane 20 does not rotate and the resultant tearing force breaks the lower portion 40 apart from the rest of the membrane 20. The aligner 38 is connected to the wall 13 in such a manner that it can move vertically, for instance with a protrusion in a slot in the wall (not shown), enabling the lower portion 40 to move downwards with the rotation of the threaded lower section 36 of the plunger 16, creating a physical gap in the membrane 20. When the plunger 16 is subsequently depressed, the lower portion 40 is able to break the barrier 28 and interact with the at least one reagent 18; however, the break in the membrane 20 prevents any reaction fluid from travelling up to the wick 24 where any excess affinity component 23 has been retained.

Referring to FIGS. 4A-4C, an assay device 400 is illustrated. In this aspect, the assay device 400 includes a receptacle 12 containing a plunger 16 and a plunger sleeve 19 disposed within the receptacle 12. The device comprises a membrane 20 attached to an exterior surface 15 of the plunger sleeve 19. The plunger sleeve 19 is configured to define an opening 42 in a portion of the plunger sleeve 19 adjacent to the detection zone 26 of the membrane 20. The plunger sleeve 19 is secured in the receptacle 12 in this embodiment by being mounted to an aligner 38 connected to a wall 13 of the receptacle 12. The aligner 38 is connected to the wall 13 in such a manner that it can move vertically, such as being in communication with a vertical slot in the wall (not shown). The detection zone 26 is attached to a surface of the plunger 16. A plurality of capture compounds 27 are immobilized on the detection zone 26. As shown in FIG. 4B, when the plunger 16 is rotated, only the detection zone 26 of the membrane 20 rotates and the resultant tearing force breaks the detection zone 26 apart from the rest of the membrane 20 and moves the detection zone 26 into the interior of the plunger sleeve 19. As shown in FIG. 4C, when the plunger 16 is subsequently depressed, the end of the plunger 30 pierces the barrier 28 and the detection zone 26 is moved through the broken barrier 28 and into fluid communication with the at least one reagent 18 contained within the receptacle 12.

Additionally, the plunger 16 may also be used to pierce a barrier in which the barrier comprises a pouch, and thus enable the simultaneous addition of extra components to the at least one reagent 18. The membrane 20 is shown arranged with the wick 24 at the bottom of the membrane 20 and a sample entry port (not shown) at the top. In this arrangement the sample fluid flows downwards. In a variation of this aspect, the assay device 400 can be simply modified so that the sample entry port is placed where the wick 24 is shown in FIGS. 4A-4B with the wick 24 to be relocated to a position above the detection zone 26. Such a device functions as a dipstick membrane, a common method in which the lower end of the membrane is immersed in the test solution. Potential sample overfilling is prevented because any excess sample added would flow back out of the port.

Figure 2B:
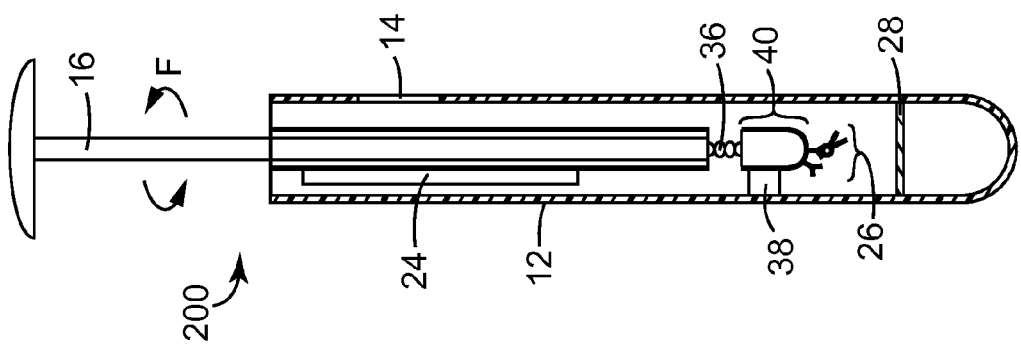
FIG. 2B is an exemplary partial cross-sectional schematic of the assay device of FIG. 2A following rotation of the plunger.
Figure 2C:
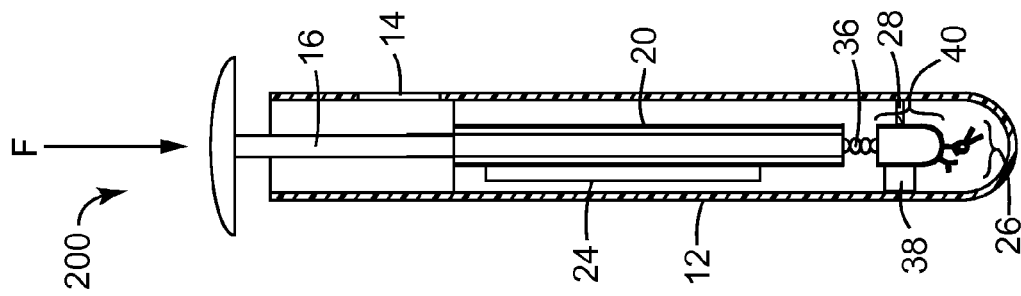
FIG. 2C is an exemplary partial cross-sectional schematic of the assay device of FIG. 2B following depression of the plunger.
Figure 3B:
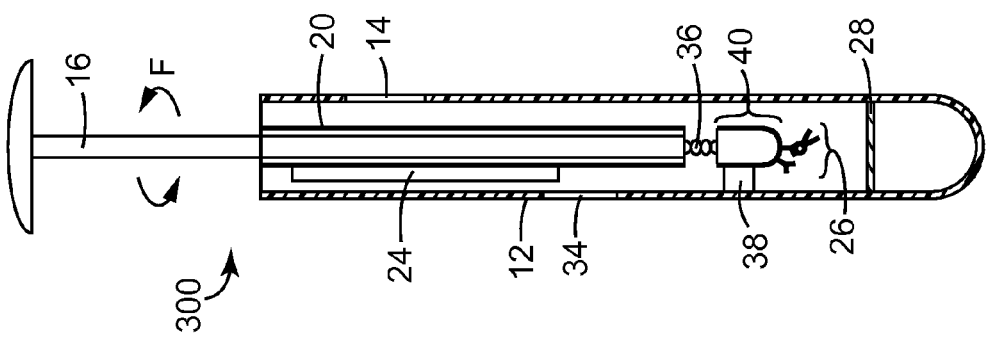
FIG. 3B is an exemplary partial cross-sectional schematic of the assay device of FIG. 3A following rotation of the plunger.
Figure 3C:
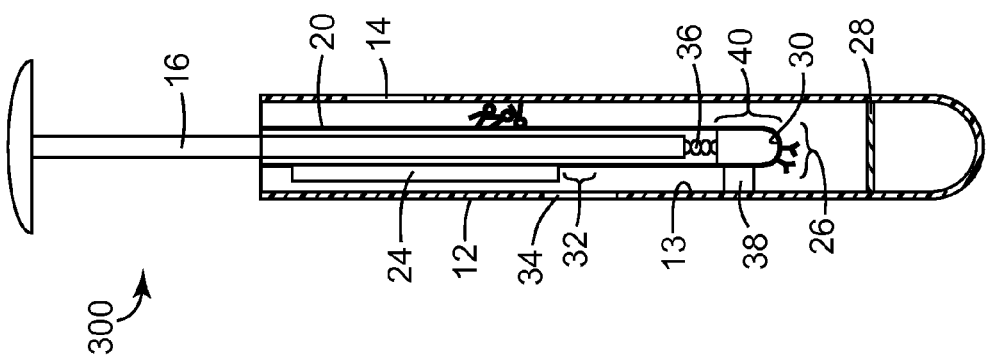
FIG. 3C is an exemplary partial cross-sectional schematic of the assay device of FIG. 3B following depression of the plunger.

Referring to each of FIGS. 2B, 3B, and 4B, in certain embodiments of the assay device, when the plunger 16 is rotated within the receptacle 12, the plunger 16 is configured to detach the detection zone 26 from being in fluid communication with the wick 24.

Figure 6A:
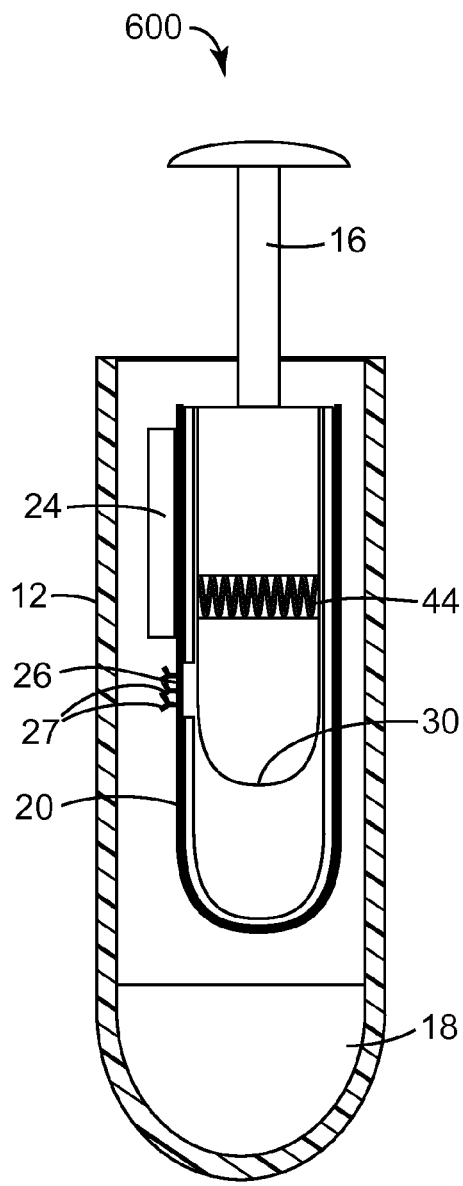
FIG. 6A is still another exemplary partial cross-sectional schematic of an assay device.
Figure 6B:
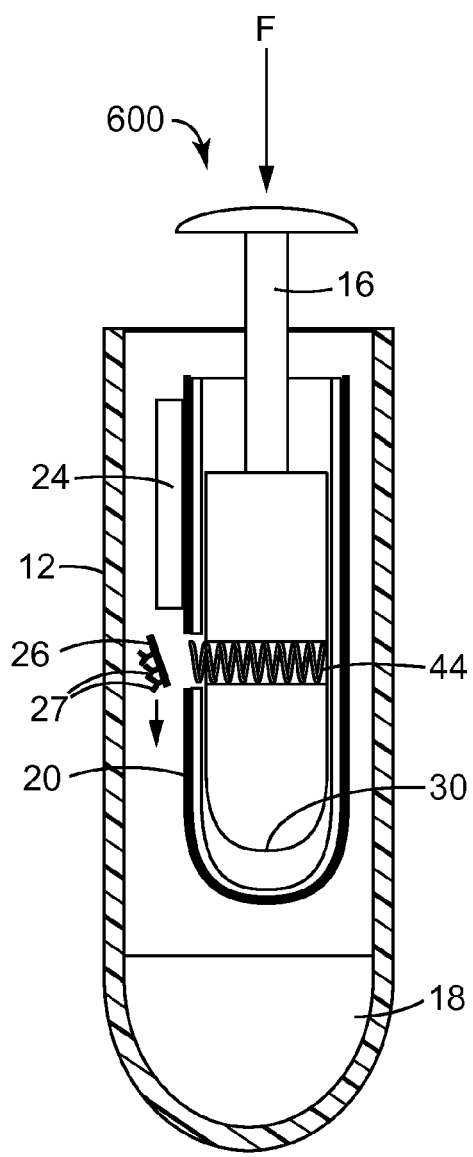
FIG. 6B is an exemplary partial cross-sectional schematic of the assay device of FIG. 6A following depression of the plunger.

Referring to FIGS. 6A and 6B, an assay device 600 is provided. The plunger 16 comprises a spring 44, wherein when the plunger 16 is depressed, the spring 44 engages with the membrane 20 at the detection zone 26 and the spring 44 expands to detach the detection zone 26 (on which a plurality of capture compounds 27 are immobilized) from being in fluid communication with the wick 24 and to place the detection zone 26 in fluid communication with the at least one reagent 18.

Referring to FIGS. 7A and 7B, an assay device 700 is provided. The plunger 16 comprises a spring 44, wherein when the plunger 16 is depressed, the spring 44 engages with the membrane 20 and the spring 44 expands to form a break in the membrane 20 at portion 21 to prevent the detection zone 26 from continuing to be in fluid communication with the wick 24. Referring to FIG. 7C, when the plunger 16 is further depressed, the detection zone 26 (on which a plurality of capture compounds 27 are immobilized) is placed in fluid communication with the at least one reagent 18. The break in the membrane 20 at portion 21 minimizes fluid flow of the at least one reagent towards the wick 24, to thereby minimize background signal during detection.

In another embodiment of an assay device (not shown), the at least one reagent is disposed inside the plunger, and the plunger is configured to release a portion of the at least one reagent to place the portion of the at least one reagent in fluid communication with the detection zone. Such a configuration avoids the use of a separate barrier to isolate the at least one reagent from the membrane.

In a further embodiment of an assay device (not shown), a portion of the receptacle is opaque and a portion of the receptacle is transparent to light. An advantage to having a portion of the receptacle be opaque is that detection of background signal beyond the portion of the receptacle transparent to light is minimized.

In a third aspect, a method for detection of a target analyte is provided, the method comprising:
 (a) providing an assay device comprising:
  a receptacle comprising a surface and a sample entry port;
  at least one reagent;
  a plunger disposed within the receptacle and having a surface;
  a membrane attached to the surface of the plunger, the surface of the receptacle, or both, the membrane comprising a wick providing capillary force; and
  a detection zone in which a plurality of capture compounds are immobilized, wherein the detection zone is located between the sample entry port and the wick;
 (b) providing a sample suspected to contain a target analyte;
 (c) adding the sample onto the membrane through the sample entry port;
 (d) allowing the sample to travel along the membrane until the sample reaches the detection zone;
 (e) immobilizing the target analyte through reaction of the target analyte with the capture compounds;
 (f) reacting the immobilized target analyte with the at least one reagent to generate a detectable signal; and
 (g) detecting the generated signal.

Any of the assay devices described in detail above with respect to the first and second aspects are suitable for use in the method of the third aspect.

In certain embodiments, the providing of the sample further comprises adding a plurality of affinity components to the sample to conjugate any target analyte, whereas in other embodiments, the membrane further comprises a target conjugate zone in which a plurality of affinity components are disposed, wherein the target conjugate zone is located between the sample entry port and the detection zone.

In most embodiments, the detection zone is attached to the surface of the plunger and/or attached to the surface of the receptacle. To react the immobilized target analyte with the at least one reagent to generate a detectable signal, the reacting further comprises applying force to the plunger to detach the detection zone from being in fluid communication with the wick and place the detection zone in fluid communication with the at least one reagent. For instance, applying force to the plunger typically comprises rotating the plunger, depressing the plunger, or rotating the plunger followed by depressing the plunger.

An advantage of the method is that it is compatible with a variety of quantitative detection methods. For example, in an embodiment the generated signal comprises luminescence and the detecting comprises using a luminometer to measure the luminescence. In another embodiment, the generated signal comprises fluorescence and the detecting comprises using a fluorimeter, and in a further embodiment the generated signal comprises a color change and the detecting comprises using a colorimeter. Preferably, the detecting further comprises quantifying the luminescence, fluorescence, or color change.

Various items are described that are assay devices or methods of detecting a target analyte using the assay devices.

Embodiment 1 is an assay device comprising a receptacle comprising a sample entry port; a plunger disposed within the receptacle and having a first surface; at least one reagent; a membrane attached to the first surface of the plunger, the membrane comprising a target conjugate zone in which a plurality of affinity components are disposed; a wick providing capillary force; and a detection zone in which a plurality of capture compounds are immobilized. The detection zone is located between the target conjugate zone and the wick.

Embodiment 2 is the assay device of embodiment 1, wherein when force is applied to the plunger, the plunger is configured to detach the detection zone from being in fluid communication with the wick and place the detection zone in fluid communication with the at least one reagent.

Embodiment 3 is the assay device of embodiment 1 or embodiment 2, wherein the at least one reagent is disposed in the receptacle.

Embodiment 4 is the assay device of any of embodiments 1 to 3, wherein the receptacle further comprises a barrier to separate the at least one reagent from the plunger.

Embodiment 5 is the assay device of embodiment 4, wherein the barrier comprises a metal foil or a pouch.

Embodiment 6 is the assay device of embodiment 4, wherein the plunger further comprises an end configured to pierce the barrier.

Embodiment 7 is the assay device of embodiment 4 or embodiment 5, wherein the plunger comprises a pointed end.

Embodiment 8 is the assay device of embodiment 1, wherein the at least one reagent is disposed inside the plunger.

Embodiment 9 is the assay device of embodiment 8, wherein the plunger is configured to release a portion of the at least one reagent to place the portion of the at least one reagent in fluid communication with the detection zone.

Embodiment 10 is the assay device of any of embodiments 1 to 9, wherein a portion of the receptacle is opaque and a portion of the receptacle is transparent to light.

Embodiment 11 is the assay device of any of embodiments 1 to 10, wherein the affinity components each comprise a binding portion comprising an antibody, a ligand, a peptide aptamer, a nucleotide aptamer, or a combination thereof.

Embodiment 12 is the assay device of any of embodiments 1 to 11, wherein the affinity components each comprise a detection portion comprising horseradish peroxidase, luciferase, alkaline phosphatase, or a combination thereof.

Embodiment 13 is the assay device of any of embodiments 1 to 12, wherein the capture compounds comprise an aptamer, a peptide, an antibody, a ligand, or a combination thereof.

Embodiment 14 is the assay device of any of embodiments 1 to 13, wherein the at least one reagent comprises hydrogen peroxide.

Embodiment 15 is the assay device of any of embodiments 1 to 14, wherein the at least one reagent comprises luciferin.

Embodiment 16 is the assay device of embodiment 15, wherein the barrier comprises a pouch and the pouch contains luminol.

Embodiment 17 is the assay device of any of embodiments 1 to 16, wherein the affinity components comprise an enzyme conjugated to a peptide aptamer or a nucleotide aptamer.

Embodiment 18 is the assay device of any of embodiments 1 to 16, wherein the affinity components comprise an enzyme conjugated to an antibody.

Embodiment 19 is the assay device of any of embodiments 1 to 18, wherein the at least one reagent comprises an aqueous solution.

Embodiment 20 is the assay device of any of embodiments 1 to 19, wherein the membrane is a fluid control film.

Embodiment 21 is the assay device of any of embodiments 1 to 20, wherein the membrane comprises nitrocellulose.

Embodiment 22 is the assay device of any of embodiments 1 to 21, wherein the detection zone comprises a nonwoven membrane.

Embodiment 23 is the assay device of any of embodiments 1 to 7 or 10 to 22, wherein when the plunger is rotated within the receptacle, the plunger is configured to detach the detection zone from being in fluid communication with the wick.

Embodiment 24 is the assay device of any of embodiments 1 to 18, wherein the plunger further comprises a second surface opposite the first surface and an end in communication with the first surface and the second surface, wherein the membrane is in contact with the end and with the second surface.

Embodiment 25 is the assay device of embodiment 24, wherein the detection zone is located at the end of the plunger.

Embodiment 26 is the assay device of any of embodiments 1 to 25, wherein the membrane further comprises a control line disposed between the wick and the detection zone, the control line comprising a generic capture compound.

Embodiment 27 is the assay device of any of embodiments 1 to 26, wherein the receptacle comprises a test tube.

Embodiment 28 is the assay device of any of embodiments 1 to 27, wherein the plunger comprises a spring, wherein when the plunger is depressed, the spring engages with the membrane at the detection zone and the spring expands to detach the detection zone from being in fluid communication with the wick and to place the detection zone in fluid communication with the at least one reagent.

Embodiment 29 is the assay device of any of embodiments 1 to 27, wherein the membrane comprises a capillary fluid conductor.

Embodiment 30 is the assay device of embodiment 29, wherein the capillary fluid conductor comprises a stacked fluid transport film.

Embodiment 31 is an assay device comprising a receptacle comprising a surface and a sample entry port; a membrane attached to the surface of the receptacle, the membrane comprising a wick providing capillary force; at least one reagent disposed in the receptacle; a plunger disposed within the receptacle and having a surface; and a detection zone in which a plurality of capture compounds are immobilized, the detection zone attached to the surface of the plunger; wherein the detection zone is located between the sample entry port and the wick.

Embodiment 32 is the assay device of embodiment 31, wherein when a force is applied to the plunger, the detection zone is moved from being in fluid communication with the membrane to being in fluid communication with the reagent.

Embodiment 33 is the assay device of embodiment 31 or embodiment 32, wherein a portion of the receptacle is opaque and a portion of the receptacle is transparent to light.

Embodiment 34 is the assay device of any of embodiments 31 to 33, wherein the affinity components each comprise a binding portion comprising an antibody, a ligand, a peptide aptamer, a nucleotide aptamer, or a combination thereof.

Embodiment 35 is the assay device of any of embodiments 31 to 34, wherein the affinity components each comprise a detection portion comprising horseradish peroxidase, luciferase, alkaline phosphatase, or a combination thereof.

Embodiment 36 is the assay device of any of embodiments 31 to 35, wherein the capture compounds comprise an aptamer, a peptide, an antibody, a ligand, or a combination thereof.

Embodiment 37 is the assay device of any of embodiments 31 to 36, wherein the at least one reagent comprises hydrogen peroxide.

Embodiment 38 is the assay device of any of embodiments 31 to 37, wherein the at least one reagent comprises luciferin.

Embodiment 39 is the assay device of any of embodiments 31 to 38, wherein the affinity components comprise an enzyme conjugated to a peptide aptamer or a nucleotide aptamer.

Embodiment 40 is the assay device of any of embodiments 31 to 38, wherein the affinity components comprise an enzyme conjugated to an antibody.

Embodiment 41 is the assay device of any of embodiments 31 to 40, wherein the at least one reagent comprises an aqueous solution.

Embodiment 42 is the assay device of any of embodiments 31 to 41, wherein the membrane is a fluid control film.

Embodiment 43 is the assay device of any of embodiments 31 to 42, wherein the membrane comprises nitrocellulose.

Embodiment 44 is the assay device of any of embodiments 31 to 43, wherein the detection zone comprises a nonwoven membrane.

Embodiment 45 is the assay device of any of embodiments 31 to 44, wherein when the plunger is rotated within the receptacle, the plunger is configured to detach the detection zone from being in fluid communication with the wick and place the detection zone in fluid communication with the at least one reagent.

Embodiment 46 is the assay device of any of embodiments 31 to 45, wherein the receptacle further comprises a barrier to separate the at least one reagent from the plunger.

Embodiment 47 is the assay device of embodiment 46, wherein the barrier comprises a metal foil or a pouch.

Embodiment 48 is the assay device of embodiment 47, wherein the plunger further comprises an end configured to pierce the barrier.

Embodiment 49 is the assay device of embodiment 47 or embodiment 48, wherein the plunger comprises a pointed end.

Embodiment 50 is the assay device of embodiment 38, wherein the barrier comprises a pouch and the pouch contains luminol.

Embodiment 51 is the assay device of any of embodiments 31 to 50, wherein the membrane further comprises a control line disposed between the wick and the detection zone, the control line comprising a generic capture compound.

Embodiment 52 is the assay device of any of embodiments 31 to 51, wherein the receptacle comprises a test tube.

Embodiment 53 is a method for detection of a target analyte, the method comprising (a) providing an assay device comprising a receptacle comprising a surface and a sample entry port; at least one reagent; a plunger disposed within the receptacle and having a surface; a membrane attached to the surface of the plunger, the surface of the receptacle, or both, the membrane comprising a wick providing capillary force; and a detection zone in which a plurality of capture compounds are immobilized, wherein the detection zone is located between the sample entry port and the wick; (b) providing a sample suspected to contain a target analyte; (c) adding the sample onto the membrane through the sample entry port; (d) allowing the sample to travel along the membrane until the sample reaches the detection zone; (e) immobilizing the target analyte through reaction of the target analyte with the capture compounds; (f) reacting the immobilized target analyte with the at least one reagent to generate a detectable signal; and (g) detecting the generated signal.

Embodiment 54 is the method of embodiment 53, wherein the providing the sample further comprises adding a plurality of affinity components to the sample to conjugate any target analyte.

Embodiment 55 is the method of embodiment 53, wherein the membrane further comprises a target conjugate zone in which a plurality of affinity components are disposed, the target conjugate zone located between the sample entry port and the detection zone.

Embodiment 56 is the method of any of embodiments 53 to 55, wherein the reacting further comprises applying force to the plunger to detach the detection zone from being in fluid communication with the wick and place the detection zone in fluid communication with the at least one reagent.

Embodiment 57 is the method of embodiment 56, wherein applying force to the plunger comprises rotating the plunger.

Embodiment 58 is the method of embodiment 56, wherein applying force to the plunger comprises depressing the plunger.

Embodiment 59 is the method of any of embodiments 53 to 58, wherein the detection zone is attached to the surface of the plunger.

Embodiment 60 is the method of any of embodiments 53 to 58, wherein the detection zone is attached to the surface of the receptacle.

Embodiment 61 is the method of any of embodiments 53 to 60, wherein the generated signal comprises luminescence and wherein the detecting comprises using a luminometer to measure the luminescence.

Embodiment 62 is the method of embodiment 61, wherein the detecting further comprises quantifying the luminescence.

Embodiment 63 is the method of any of embodiments 53 to 60, wherein the generated signal comprises fluorescence.

Embodiment 64 is the method of embodiment 63, wherein the detecting further comprises quantifying the fluorescence.

Embodiment 65 is the method of any of embodiments 53 to 60, wherein the generated signal comprises a color change.

Embodiment 66 is the method of embodiment 65, wherein the detecting further comprises quantifying the color change.

Embodiment 67 is the method of any of embodiments 53 to 66, wherein a portion of the receptacle is opaque and a portion of the receptacle is transparent to light.

Embodiment 68 is the method of any of embodiments 53 to 67, wherein the affinity components each comprise a binding portion comprising an antibody, a ligand, a peptide aptamer, a nucleotide aptamer, or a combination thereof.

Embodiment 69 is the method of any of embodiments 53 to 68, wherein the affinity components each comprise a detection portion comprising horseradish peroxidase, luciferase, alkaline phosphatase, or a combination thereof.

Embodiment 70 is the method of any of embodiments 53 to 69, wherein the capture compounds comprise an aptamer, a peptide, an antibody, a ligand, or a combination thereof.

Embodiment 71 is the method of any of embodiments 53 to 70, wherein the at least one reagent comprises hydrogen peroxide.

Embodiment 72 is the method of any of embodiments 53 to 71, wherein the at least one reagent comprises luciferin.

Embodiment 73 is the method of any of embodiments 53 to 71, wherein the affinity components comprise an enzyme conjugated to a peptide aptamer or a nucleotide aptamer.

Embodiment 74 is the method of any of embodiments 53 to 71, wherein the affinity components comprise an enzyme conjugated to an antibody.

Embodiment 75 is the method of any of embodiments 53 to 74, wherein the at least one reagent comprises an aqueous solution.

Embodiment 76 is the method of any of embodiments 53 to 75, wherein the membrane is a fluid control film.

Embodiment 77 is the method of any of embodiments 53 to 76, wherein the membrane comprises nitrocellulose.

Embodiment 78 is the method of any of embodiments 53 to 77, wherein the detection zone comprises a nonwoven membrane.

Embodiment 79 is the method of any of embodiments 53 to 78, wherein when the plunger is rotated within the receptacle, the plunger is configured to detach the detection zone from being in fluid communication with the wick and place the detection zone in fluid communication with the at least one reagent.

Embodiment 80 is the method of embodiment 53, wherein the at least one reagent is disposed in the receptacle.

Embodiment 81 is the method of any of embodiments 53 to 80, wherein the receptacle further comprises a barrier to separate the at least one reagent from the plunger.

Embodiment 82 is the method of embodiment 81, wherein the barrier comprises a metal foil or a pouch.

Embodiment 83 is the method of embodiment 82, wherein the barrier comprises a pouch and the pouch contains luminol.

Embodiment 84 is the method of embodiment 82, wherein the plunger further comprises an end configured to pierce the barrier.

Embodiment 85 is the method of embodiment 82 or embodiment 83, wherein the plunger comprises a pointed end.

Embodiment 86 is the method of embodiment 53, wherein the at least one reagent is disposed inside the plunger.

Embodiment 87 is the method of embodiment 86, wherein the plunger is configured to release a portion of the at least one reagent to place the portion of the at least one reagent in fluid communication with the detection zone.

Embodiment 88 is the method of any of embodiments 53 to 87, wherein the plunger further comprises a second surface opposite the first surface and an end in communication with the first surface and the second surface, wherein the membrane is in contact with the end and with the second surface.

Embodiment 89 is the method of embodiment 88, wherein the detection zone is located at the end of the plunger.

Embodiment 90 is the method of any of embodiments 53 to 89, wherein the membrane further comprises a control line disposed between the wick and the detection zone, the control line comprising a generic capture compound.

Embodiment 91 is the method of any of embodiments 53 to 90, wherein the receptacle comprises a test tube.

Embodiment 92 is the method of any of embodiments 53 to 91, wherein the plunger comprises a spring, wherein when the plunger is depressed, the spring engages with the membrane at the detection zone and the spring expands to detach the detection zone from being in fluid communication with the wick and to place the detection zone in fluid communication with the at least one reagent.

Embodiment 93 is the method of any of embodiments 53 to 92, wherein the membrane comprises a capillary fluid conductor.

Embodiment 94 is the method of embodiment 93, wherein the capillary fluid conductor comprises a stacked fluid transport film.

EXAMPLES

Objects and advantages of this invention are further illustrated by the following examples, but the particular materials and amounts thereof recited in these examples, as well as other conditions and details, should not be construed to unduly limit this invention. These examples are for illustrative purposes only and are not meant to be limiting on the scope of the appended claims.

Materials

Unless otherwise noted, all parts, percentages, ratios, etc., in the examples and in the remainder of the specification are by weight. Unless otherwise noted, all chemicals are available from chemical suppliers such as Sigma-Aldrich Chemical Company, St. Louis, Mo.

Example 1-1

Aptamers that bind specifically to Penicillin G are conjugated with horseradish peroxidase (HRP) and deposited on a fluid transport film affixed to the surface of the plunger. Capture antibodies to Penicillin G are deposited on the detection zone. Luminol is contained within a foil pouch positioned below the plunger and separating the plunger from a reagent solution containing hydrogen peroxide and, optionally, a surfactant. A 100 μL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer (3M Company, St. Paul, Minn.).

Example 1-2

Aptamers that bind specifically to Penicillin G are conjugated with horseradish peroxidase (HRP) and deposited on a fluid transport film affixed to the surface of the plunger. Capture antibodies to Penicillin G are deposited on the detection zone. ABTS (2,2'-azinobis [3-ethylbenzothiazoline-6-sulfonic acid]-diammonium salt) is contained within a foil pouch positioned below the plunger and separating the plunger from a reagent solution containing hydrogen peroxide and, optionally, a surfactant. A 200 μL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing the ABTS contained within the pouch to contact the reagent solution. HRP retained in the detection zone oxidizes the colorless ABTS to its blue radical cation. The intensity of the blue color can be assessed visually by comparison with a color chart, or with a colorimeter such as the 3M CLEAN-TRACE colorimeter (3M Company, St. Paul, Minn.).

Example 1-3

Aptamers that bind specifically to Penicillin G are conjugated with horseradish peroxidase (HRP) and deposited on a fluid transport film affixed to the surface of the plunger. Capture antibodies to Penicillin G are deposited on the detection zone. ADHP (10-acetyl-3,7-dihydroxyphenoxazine) is contained within a foil pouch positioned below the plunger and separating the plunger from a reagent solution containing hydrogen peroxide and, optionally, a surfactant. A 250 μL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing the ADHP contained within the pouch to contact the reagent solution. HRP retained in the detection zone oxidizes the nonfluorescent ADHP to highly fluorescent resorufin. The intensity of the fluorescence can be assessed visually by irradiation with a standard UV lamp, or preferably with a fluorimeter using an excitation wavelength at of ~570 nm and emission of ~585 nm.

Example 1-4

Aptamers that bind specifically to Penicillin G are conjugated with horseradish peroxidase (HRP) and deposited on a fluid transport film affixed to the surface of the plunger. Capture antibodies to Penicillin G are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. A 1 mL aliquot of pH 7 buffer is then added through the sample entry port in order to rinse the fluid transport film and detection zone of excess HRP-conjugated antibodies. After 5 minutes, the plunger is depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer (3M Company, St. Paul, Minn.).

Example 1-5

Aptamers that bind specifically to Penicillin G are conjugated with horseradish peroxidase (HRP) and deposited on a fluid transport film affixed to the surface of the plunger. Capture antibodies to Penicillin G are deposited on the detection zone. ABTS (2,2'-azinobis [3-ethylbenzothiazoline-6-sulfonic acid]-diammonium salt) is contained within a foil pouch positioned below the plunger and separating the plunger from a reagent solution containing hydrogen peroxide and, optionally, a surfactant. A 200 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. A 1 mL aliquot of pH 7 buffer is then added through the sample entry port in order to rinse the fluid transport film and detection zone of excess HRP-conjugated antibodies. After 5 minutes, the plunger is depressed, puncturing the foil seal and allowing the ABTS contained within the pouch to contact the reagent solution. HRP retained in the detection zone oxidizes the colorless ABTS to its blue radical cation. The intensity of the blue color can be assessed visually by comparison with a color chart, or with a colorimeter such as the 3M CLEAN-TRACE colorimeter (3M Company, St. Paul, Minn.).

Example 1-6

Aptamers that bind specifically to Penicillin G are conjugated with horseradish peroxidase (HRP) and deposited on a fluid transport film affixed to the surface of the plunger. Capture antibodies to Penicillin G are deposited on the detection zone. ADHP (10-acetyl-3,7-dihydroxyphenoxazine) is contained within a foil pouch positioned below the plunger and separating the plunger from a reagent solution containing hydrogen peroxide and, optionally, a surfactant. A 250 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. A 1 mL aliquot of pH 7 buffer is then added through the sample entry port in order to rinse the fluid transport film and detection zone of excess HRP-conjugated antibodies. After 5 minutes, the plunger is depressed, puncturing the foil seal and allowing the ADHP contained within the pouch to contact the reagent solution. HRP retained in the detection zone oxidizes the nonfluorescent ADHP to highly fluorescent resorufin. The intensity of the fluorescence can be assessed visually by irradiation with a standard UV lamp, or preferably with a fluorimeter using an excitation wavelength at of ~570 nm and emission of ~585 nm.

Example 2-1

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side. During this time, any *c. diff* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 2-2

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side. During this time, any *c. diff* present in the sample has sufficient time to react with the HRP-conjugated antibodies, travel along the film and then bind to the capture antibody where it will be retained in the detection zone. A 1 mL aliquot of pH 7 buffer is then added through the sample entry port in order to rinse the fluid transport film and detection zone of excess HRP-conjugated antibodies. After 5 minutes, the plunger is rotated one full turn to cause a break in the fluid path of the membrane. The plunger is then depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 2-3

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side. During this time, any *c. diff* present in the sample has sufficient time to react with the HRP-conjugated antibodies, travel along the film and then bind to the capture antibody where it will be retained in the detection zone. A 1 mL aliquot of pH 5 buffer is then added through the sample entry port in order to rinse the fluid transport film and detection zone of excess HRP-conjugated antibodies. After 5 minutes, the plunger is rotated one full turn to cause a break in the fluid path of the membrane. The plunger is then depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 2-4

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side. During this time, any *c. diff* present in the sample has sufficient time to react with the HRP-conjugated antibodies, travel along the film and then bind to the capture antibody where it will be retained in the detection zone. A 1 mL aliquot of pH 9 buffer is then added through the sample entry port in order to rinse the fluid transport film and detection zone of excess HRP-conjugated antibodies. After 5 minutes, the plunger is rotated one full turn to cause a break in the fluid path of the membrane. The plunger is then depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 2-5

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. ABTS (2,2'-azinobis [3-ethylbenzothiazoline-6-sulfonic acid]-diammonium salt) is contained within a foil pouch positioned below the plunger and separating the plunger from a reagent solution containing hydrogen peroxide and, optionally, a surfactant. A 400 µL aliquot of the sample solution is introduced via a pipet through the sample entry port of the receptacle, and allowed to wick along the fluid transport film until it reaches the wick on the other side. During this time, any *c. diff* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing ABTS contained within the pouch to contact the reagent solution. HRP retained in the detection zone oxidizes the colorless ABTS to its blue radical cation. The intensity of the blue color can be assessed visually by comparison with a color chart, or with a colorimeter such as the 3M CLEAN-TRACE Colorimeter.

Example 2-6

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. ADHP (10-acetyl-3,7-dihydroxyphenoxazine) is contained within a foil pouch positioned below the plunger and separating the plunger from a reagent solution containing hydrogen peroxide and, optionally, a surfactant. A 800 µL aliquot of the sample solution is introduced via a pipet through the sample entry port of the receptacle, and allowed to wick along the fluid transport film until it reaches the wick on the other side. During this time, any *c. diff.* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing ADHP contained within the pouch to contact the reagent solution. HRP retained in the detection zone oxidizes the nonfluorescent ADHP to highly fluorescent resorufin. The intensity of the fluorescence can be assessed visually by irradiation with a standard UV lamp, or preferably with a fluorimeter using an excitation wavelength at of ~570 nm and emission of ~585 nm.

Example 3-1

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. Luminol is contained within a foil pouch positioned below the plunger and separating the plunger from a reagent solution containing hydrogen peroxide and, optionally, a surfactant. The wick contains a small amount of bromophenol blue, in its yellow, acid form. A 250 µL aliquot of the sample solution is mixed with 1 mL of pH 7 buffer and introduced via a pipet through the sample entry port of the receptacle, and allowed to wick along the fluid transport film until it reaches the wick on the other side. This is demonstrated by the appearance of a blue color (due to bromophenol blue) on the wick which may be visualized through the window. During this time, any *c. diff* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 3-2

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. ABTS (2,2'-azinobis [3-ethylbenzothiazoline-6-sulfonic acid]-diammonium salt) is contained within a foil pouch positioned below the plunger and separating the plunger from a reagent solution containing hydrogen peroxide and, optionally, a surfactant. The wick contains a small amount of bromophenol blue, in its yellow, acid form. A 100 µL aliquot of the sample solution is mixed with 1 mL of pH 7 buffer and introduced via a pipet through the sample entry port of the receptacle, and allowed to wick along the fluid transport film until it reaches the wick on the other side. This is demonstrated by the appearance of a blue color (due to bromophenol blue) on the wick which may be visualized through the window. During this time, any *c. diff* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing ABTS contained within the pouch to contact the reagent solution. HRP retained in the detection zone oxidizes the colorless ABTS to its blue radical cation. The intensity of the blue color can be assessed visually by comparison with a color chart, or with a colorimeter such as the 3M CLEAN-TRACE Colorimeter.

Example 3-3

Antibodies to *clostridium difficile* as described in U.S. Pat. No. 8,697,374 are conjugated with horseradish peroxidase (HRP) and deposited on a nitrocellulose membrane affixed to the surface of the plunger. Capture antibodies to *clostridium difficile* are deposited on the detection zone. ADHP (10-acetyl-3,7-dihydroxyphenoxazine) is contained within a foil pouch positioned below the plunger and separating the plunger from a reagent solution containing hydrogen peroxide and, optionally, a surfactant. The wick contains a small amount of bromophenol blue, in its yellow, acid form. A 250 µL aliquot of the sample solution is mixed with 1 mL of pH 7 buffer and introduced via a pipet through the sample entry port of the receptacle, and allowed to wick along the fluid transport film until it reaches the wick on the other side. This is demonstrated by the appearance of a blue color (due to bromophenol blue) on the wick which may be visualized through the window. During this time, any *c. diff* present in the sample has sufficient time to react with the HRP-conjugated antibodies, travel along the film and then bind to the capture antibody where it will be retained in the detection zone. After 5 minutes, the plunger is rotated one full turn to cause a break in the fluid path of the membrane. The plunger is then depressed, puncturing the foil seal and allowing ADHP contained within the pouch to contact the reagent solution. HRP retained in the detection zone oxidizes the nonfluorescent ADHP to highly fluorescent resorufin. The intensity of the fluorescence can be assessed visually by irradiation with a standard UV lamp, or preferably with a fluorimeter using an excitation wavelength at of ~570 nm and emission of ~585 nm.

Example 4-1

Aflatoxin-binding peptides are conjugated with horseradish peroxidase (HRP) and deposited on a nitrocellulose membrane affixed to the surface of the plunger. Capture antibodies to aflatoxin are deposited on the detection zone. The detection zone is bounded on either side by two weakened regions (for example perforations) which do not inhibit fluid transport but which will break when physically stressed. Luminol is contained within a foil pouch positioned below the plunger and separating the plunger from a reagent solution containing hydrogen peroxide and, optionally, a surfactant. The wick contains a small amount of bromophenol blue, in its yellow, acid form. A 50 µL aliquot of the sample solution is mixed with 0.5 mL of pH 7 buffer and introduced via a pipet through the sample entry port of the receptacle, and allowed to wick down the fluid transport film until it reaches the wick below. This is demonstrated by the appearance of a blue color (due to bromophenol blue) on the wick which may be visualized through the window. During this time, any aflatoxin present in the sample has sufficient time to react with the HRP-conjugated peptides, travel along the film and then bind to the capture antibody where it will be retained in the detection zone. After 5 minutes, the plunger is rotated one quarter turn to cause a break in the fluid path of the membrane. The plunger is then depressed, puncturing the foil seal and allowing luminol contained within the pouch to contact the reagent solution and moving the detection zone of the membrane down into the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 4-2

Aflatoxin-binding peptides are conjugated with horseradish peroxidase (HRP) and deposited on a nitrocellulose membrane affixed to the surface of the plunger. Capture antibodies to aflatoxin are deposited on the detection zone. The detection zone is bounded on either side by two weakened regions (for example perforations) which do not inhibit fluid transport but which will break when physically stressed. Luminol is contained within a foil pouch positioned below the plunger and separating the plunger from a reagent solution containing hydrogen peroxide and, optionally, a surfactant. The wick contains a small amount of bromophenol blue, in its yellow, acid form. A 50 µL aliquot of the sample solution is mixed with 0.5 mL of pH 8 buffer and introduced via a pipet through the sample entry port of the receptacle, and allowed to wick down the fluid transport film until it reaches the wick below. This is demonstrated by the appearance of a blue color (due to bromophenol blue) on the wick which may be visualized through the window. During this time, any aflatoxin present in the sample has sufficient time to react with the HRP-conjugated peptides, travel along the film and then bind to the capture antibody where it will be retained in the detection zone. After 5 minutes, the plunger is rotated one quarter turn to cause a break in the fluid path of the membrane. The plunger is then depressed, puncturing the foil seal and allowing luminol contained within the pouch to contact the reagent solution and moving the detection zone of the membrane down into the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 4-3

Aflatoxin-binding peptides are conjugated with horseradish peroxidase (HRP) and deposited on a nitrocellulose membrane affixed to the surface of the plunger. Capture antibodies to aflatoxin are deposited on the detection zone. The detection zone is bounded on either side by two weakened regions (for example perforations) which do not inhibit fluid transport but which will break when physically stressed. Luminol is contained within a foil pouch positioned below the plunger and separating the plunger from a reagent solution containing hydrogen peroxide and, optionally, a surfactant. The wick contains a small amount of bromophenol blue, in its yellow, acid form. A 50 µL aliquot of the sample solution is mixed with 0.5 mL of pH 9 buffer and introduced via a pipet through the sample entry port of the receptacle, and allowed to wick down the fluid transport film until it reaches the wick below. This is demonstrated by the appearance of a blue color (due to bromophenol blue) on the wick which may be visualized through the window. During this time, any aflatoxin present in the sample has sufficient time to react with the HRP-conjugated peptides, travel along the film and then bind to the capture antibody where it will be retained in the detection zone. After 5 minutes, the plunger is rotated one quarter turn to cause a break in the fluid path of the membrane. The plunger is then depressed, puncturing the foil seal and allowing luminol contained within the pouch to contact the reagent solution and moving the detection zone of the membrane down into the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 5-1

Tropomyosin-binding peptides are conjugated with alkaline phosphatase (AP) and deposited on a nitrocellulose membrane affixed to the surface of the plunger. Capture antibodies to tropomyosin are deposited on the detection zone. A chemiluminescent AP substrate such as CDP Star (ABI, Thermo) is contained within a reagent solution optionally containing a surfactant and/or a chemiluminescent enhancer such as Sapphire II or Emerald II. The wick contains a small amount of bromophenol blue, in its yellow, acid form. A 500 µL aliquot of the sample solution is mixed with 0.5 mL of pH 7 buffer and introduced via a pipet through the sample entry port of the receptacle, and allowed to travel up the fluid transport film until it reaches the wick at the top. This is demonstrated by the appearance of a blue color (due to bromophenol blue) on the wick which may be visualized through the window. During this time, any tropomyosin present in the sample has sufficient time to react with the AP-conjugated peptides, travel along the film and then bind to the capture antibody where it will be retained in the detection zone. After 5 minutes, the plunger is rotated one quarter turn to cause a break in the fluid path of the membrane. The plunger is then depressed, puncturing the foil seal and moving the detection zone of the membrane down into the reagent solution. Any AP retained in the detection zone hydrolyses the CDP-Star substrate with the emission of light. The light is measured by a hand-held luminometer such as the 3M CLEAN-TRACE luminometer.

Example 5-2

Tropomyosin-binding peptides are conjugated with alkaline phosphatase (AP) and deposited on a nitrocellulose membrane affixed to the surface of the plunger. Capture antibodies to tropomyosin are deposited on the detection zone. A chemiluminescent AP substrate such as CDP Star (ABI, Thermo) is contained within a reagent solution optionally containing a surfactant and/or a chemiluminescent enhancer such as Sapphire II or Emerald II. The wick contains a small amount of bromophenol blue, in its yellow, acid form. A 500 µL aliquot of the sample solution is mixed with 0.5 mL of pH 7 buffer and introduced via a pipet through the sample entry port of the receptacle, and allowed to travel up the fluid transport film until it reaches the wick at the top. This is demonstrated by the appearance of a blue color (due to bromophenol blue) on the wick which may be visualized through the window. During this time, any tropomyosin present in the sample has sufficient time to react with the AP-conjugated peptides, travel along the film and then bind to the capture antibody where it will be retained in the detection zone. After 1 minute, the plunger is rotated one quarter turn to cause a break in the fluid path of the membrane. The plunger is then depressed, puncturing the foil seal and moving the detection zone of the membrane down into the reagent solution. Any AP retained in the detection zone hydrolyses the CDP-Star substrate with the emission of light. The light is measured by a hand-held luminometer such as the 3M CLEAN-TRACE luminometer.

Example 5-3

Tropomyosin-binding peptides are conjugated with alkaline phosphatase (AP) and deposited on a nitrocellulose membrane affixed to the surface of the plunger. Capture antibodies to tropomyosin are deposited on the detection zone. A chemiluminescent AP substrate such as CDP Star (ABI, Thermo) is contained within a reagent solution optionally containing a surfactant and/or a chemiluminescent enhancer such as Sapphire II or Emerald II. The wick contains a small amount of bromophenol blue, in its yellow, acid form. A 500 µL aliquot of the sample solution is mixed with 0.5 mL of pH 7 buffer and introduced via a pipet through the sample entry port of the receptacle, and allowed to travel up the fluid transport film until it reaches the wick at the top. This is demonstrated by the appearance of a blue color (due to bromophenol blue) on the wick which may be visualized through the window. During this time, any tropomyosin present in the sample has sufficient time to react with the AP-conjugated peptides, travel along the film and then bind to the capture antibody where it will be retained in the detection zone. After 10 minutes, the plunger is rotated one quarter turn to cause a break in the fluid path of the membrane. The plunger is then depressed, puncturing the foil seal and moving the detection zone of the membrane down into the reagent solution. Any AP retained in the detection zone hydrolyses the CDP-Star substrate with the emission of light. The light is measured by a hand-held luminometer such as the 3M CLEAN-TRACE luminometer.

Example 6-1

Aptamers that bind specifically to Penicillin G are conjugated with horseradish peroxidase (HRP) and deposited on a fluid transport film affixed to the surface of the receptacle. Capture antibodies to Penicillin G are deposited on the detection zone. Luminol is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing luminol contained within the pouch to contact the reagent solution. Any HRP retained in the detection zone facilitates the oxidation of luminol by hydrogen peroxide and generates 3-aminophthalate with the emission of light. The light is measured by a hand-held luminometer such as the 3M CLEAN-TRACE luminometer.

Example 6-2

Aptamers that bind specifically to Penicillin G are conjugated with horseradish peroxidase (HRP) and deposited on a fluid transport film affixed to the surface of the receptacle. Capture antibodies to Penicillin G are deposited on the detection zone. ABTS (2,2'-azinobis [3-ethylbenzothiazoline-6-sulfonic acid]-diammonium salt) is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing the ABTS contained within the pouch to contact the reagent solution. HRP retained in the detection zone oxidizes the colorless ABTS to its blue radical cation. The intensity of the blue color can be assessed visually by comparison with a color chart, or with a colorimeter such as the 3M CLEAN-TRACE Colorimeter.

Example 6-3

Aptamers that bind specifically to Penicillin G are conjugated with horseradish peroxidase (HRP) and deposited on a fluid transport film affixed to the surface of the receptacle. Capture antibodies to Penicillin G are deposited on the detection zone. ADHP (10-acetyl-3,7-dihydroxyphenoxazine) is contained within a foil pouch positioned below the plunger and separating the plunger from a reagent solution containing hydrogen peroxide and, optionally, a surfactant. A 100 µL aliquot of the sample solution is introduced via a pipet through the sample entry port of the receptacle, and allowed to wick along the fluid transport film until it reaches the wick on the other side, typically 5 minutes. During this time, any Penicillin G present in the sample has sufficient time to react with the HRP-conjugated aptamers, travel along the film and then bind to the capture antibody where it will be retained in the detection zone. After 5 minutes, the plunger is depressed, puncturing the foil seal and allowing the ADHP contained within the pouch to contact the reagent solution. HRP retained in the detection zone oxidizes the nonfluorescent ADHP to highly fluorescent resorufin. The intensity of the fluorescence can be assessed visually by irradiation with a standard UV lamp, or preferably with a fluorimeter using an excitation wavelength at of ~570 nm and emission of ~585 nm.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A assay device comprising:
   a receptacle comprising a sample entry port;
   a plunger disposed within the receptacle and having a first surface;
   at least one reagent;
   a membrane attached to the first surface of the plunger, the membrane comprising:
   a target conjugate zone in which a plurality of affinity components are disposed;
   a wick providing capillary force; and
   a detection zone in which a plurality of capture compounds are immobilized,
   wherein the detection zone is located between the target conjugate zone and the wick, wherein the plunger comprises a spring, wherein when the plunger is depressed, the spring engages with the membrane at the detection zone and the spring expands to detach the detection zone from being in fluid communication with the wick and to place the detection zone in fluid communication with the at least one reagent.

2. The assay device of claim 1, wherein the at least one reagent is disposed in the receptacle.

3. The assay device of claim 1, wherein the receptacle further comprises a barrier to separate the at least one reagent from the plunger.

4. The assay device of claim 1, wherein the affinity components each comprise a binding portion comprising an antibody, a ligand, a peptide aptamer, a nucleotide aptamer, or a combination thereof.

5. The assay device of claim 1, wherein the capture compounds comprise an aptamer, a peptide, an antibody, a ligand, or a combination thereof.

6. The assay device of claim 1, wherein the plunger further comprises a second surface opposite the first surface and an end in communication with the first surface and the second surface, wherein the membrane is in contact with the end and with the second surface.

7. The assay device of claim 1, wherein the receptacle comprises a test tube.

\* \* \* \* \*

UNITED STATES PATENT AND TRADEMARK OFFICE
CERTIFICATE OF CORRECTION

| | | |
|---|---|---|
| PATENT NO. | : 9,987,633 B2 | Page 1 of 1 |
| APPLICATION NO. | : 15/309505 | |
| DATED | : June 5, 2018 | |
| INVENTOR(S) | : Stephen Roscoe | |

It is certified that error appears in the above-identified patent and that said Letters Patent is hereby corrected as shown below:

On the Title Page

Column 1,
Line 3, after "0 days." delete "days.".

In the Specification

Column 18,
Line 41, delete "diff" and insert -- diff. --, therefor.

Column 19,
Line 1, delete "diff" and insert -- diff. --, therefor.
Line 31, delete "diff" and insert -- diff. --, therefor.
Line 61, delete "diff" and insert -- diff. --, therefor.

Column 20,
Line 26, delete "diff" and insert -- diff. --, therefor.

Column 21,
Line 18, delete "diff" and insert -- diff. --, therefor.
Line 50, delete "diff" and insert -- diff. --, therefor.

Column 22,
Line 14, delete "diff" and insert -- diff. --, therefor.

Signed and Sealed this
Twenty-eighth Day of August, 2018

Andrei Iancu
*Director of the United States Patent and Trademark Office*